US00PP11633P

United States Patent [19]

Zary

[11] Patent Number: Plant 11,633

[45] Date of Patent: Nov. 14, 2000

[54] HYBRID TEA ROSE PLANT NAMED 'JACFANGO'

[75] Inventor: Keith W. Zary, Thousand Oaks, Calif.

[73] Assignee: Bear Creek Gardens, Inc., Medford, Oreg.

[21] Appl. No.: 09/234,788

[22] Filed: Jan. 20, 1999

[51] Int. Cl.[7] ..... A01H 5/00

[52] U.S. Cl. ..... Plt./134

[58] Field of Search ..... Plt./133, 134

[56] References Cited

U.S. PATENT DOCUMENTS

P.P. 11,272 3/2000 Segers ..... Plt./134

*Primary Examiner*—Howard J. Locker

*Attorney, Agent, or Firm*—Klarquist Sparkman Campbell Leigh & Whinston, LLP

[57] ABSTRACT

Hybrid tea rose plant having novel yellow bud and flower color, good production of long stemmed, cut flowers having excellent vase life and resistance to powdery mildew.

1 Drawing Sheet

The present invention relates to a new and distinct variety of rose plant of the hybrid tea rose class which was originated by me by crossing the variety 'JACpow', U.S. Plant Pat. No. 8,646, with the variety 'JACgold', U.S. Plant Pat. No. 5,121.

The primary objective of this breeding was to produce a new rose variety having the large flowers, long buds, and long stems of the female variety combined with the thick petals, resistance to powdery mildew and good vase life of the male parent. Flower color was expected to be intermediate between the parents.

The objective was substantially achieved, along with other desirable improvements, as evidenced by the following unique combination of characteristics that are outstanding in the new variety and that distinguish it from its parents, as well as from all other varieties of which I am aware:

1. Long bud;
2. Novel bud and flower color;
3. Long stems;
4. Excellent vase life;
5. Good cut flower production, and;
6. Resistant to powdery mildew.

'JACfango' is a novel colored, cut flower rose. It has a long vase life and will produce 170–180 long stem roses per $m^2$ of greenhouse.

Asexual reproduction of this new variety by budding, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.*—'JACpow' (U.S. Plant Pat. No. 8,646).

*Pollen parent.*—'JACgold' (U.S. Plant Pat. No. 5,121).

Classification:

*Botanical.*—*Rosa hybrida.*

*Commercial.*—Hybrid Tea.

FLOWER

Observations made from specimens grown in a greenhouse environment at Somis, Calif., February 1997 to December 1998.

Blooming habit: Continuous.

Bud:

*Size.*—Two and one-quarter inches long when the petals start to unfurl.

*Form.*—The bud form is long, pointed ovoid.

*Color.*—When sepals first divide, bud color is between Yellow-Green Group 145B and 145C. When half blown, the upper sides of the petals are Yellow Group 4D except for the guard petals which are close to Yellow-Green Group 154C and the lower sides of the petals are Yellow Group 4D except for the guard petals which are close to Yellow-Green Group 154C.

*Sepals.*—Color: Green Group 138B. Surface texture: Covered in fine hairs. There are three normally appendaged sepals. There are two unappendaged sepals with hairy edges.

*Receptacle.*—Color: Yellow-Green Group 146C. Shape: Funnel. Size: Medium, about 7/16"×3/8". Surface: Smooth.

*Peduncle.*—Length: Long, averaging about four and one-half inches. Surface: Glandular, with a few small prickles. Color: Yellow-Green Group 146C. Strength: Stiff, erect, heavy.

Bloom:

*Size.*—Large. Average open size is five inches.

*Borne.*—Singly.

*Stems.*—Strength: Strong. Average length is about twenty-four to twenty-eight inches.

*Form.*—When first open: High-centered. Permanence: Retains its form to the end. Outer petals curl back, with some quilling.

*Petalage.*—Number of petals under normal conditions: 45.

*Color.*—The upper sides of the petals Yellow Group 4D except for the guard petals which are close to Yellow-Green Group 154C. The reverse sides of the petals are Yellow Group 4D except for the guard petals which are close to Yellow-Green Group 154C. The base of each petal has, on the upper surface, a ¼"×¼", Yellow Group 4B color spot. The lower surface has a very small tinge of Yellow-Green Group 154C at the point of attachment. The major color on the upper side is Yellow Group 4D.

*Variegations.*—None.

*Discoloration.*—The general tonality at the end of the first day: No change. At the end of the third day: No change. No change through day fourteen in the vase.

*Fragrance.*—Moderate, spicy.

Petals:

*Texture*.—Thick.

*Shape*.—Round.

*Form*.—Tips slightly recurved, edges slightly quilled.

*Arrangement*.—Imbricated. Petaloids in the center: None.

*Persistence*.—Petals drop off cleanly before drying.

*Lastingness*.—On the plant: Long (eight to nine days). As a cut flower: Very long (about fourteen days).

Reproductive parts:

*Anthers*.—Size: Medium. Quantity: Many. Color: Yellow-Orange Group 16B. Arrangement: Regular around styles.

*Filaments*.—Color: Yellow Group 8B.

*Pollen*.—Present.

*Styles*.—Color: Green-White Group 157D.

*Stigmas*.—Color: Yellow-White Group 158C.

Plant:

*Form*.—Bush.

*Growth*.—Vigorous. Mature plant height is about six and one-half feet, width is about four feet.

Foliage: Number of leaflets on normal mid-stem leaves: Five.

*Size*.—Large (6" long×5" wide).

*Quantity*.—Abundant.

*Color*.—New foliage: Upper and lower surfaces: Greyed-Red Group 178B. Old foliage: Upper surface: Green Group 137A. Lower surface: Green Group 137C.

Leaflets:

*Shape*.—Pointed oval

*Texture*.—Leathery. .

*Edge*.—Serrated.

*Serration*.—Single, small.

*Petiole rachis*.—Yellow-Green Group 147C, often, especially on younger leaves, there is Greyed-Purple Group 183B coloration.

*Petiole underside*.—Smooth with an occasional prickle.

*Stipules*.—Medium (9/16"), serrated, bearded.

*Disease resistance*.—Resistant to mildew and rust under normal growing conditions in a greenhouse. Not tested for blackspot.

Wood:

*New wood*.—Color: Greyed-Red Group 178B. Bark: Smooth.

*Old wood*.—Color: Green Group 137B. Bark: Smooth.

Prickles:

*Quantity*.—On main canes from base: Ordinary. On laterals from main canes: Ordinary.

*Form*.—Hooked downward.

*Color when young*.—Greyed-Purple Group 183C.

*Color when mature*.—Greyed-Orange Group 174B.

Small prickles:

*Quantity*.—On main stalks: None. On laterals: None.

I claim:

1. A new and distinct variety of rose plant of the hybrid tea class, substantially as herein shown and described, characterized particularly by its novel yellow bud and flower color, its good production of long stemmed, cut flowers having excellent vase life and resistance to powdery mildew.

* * * * *

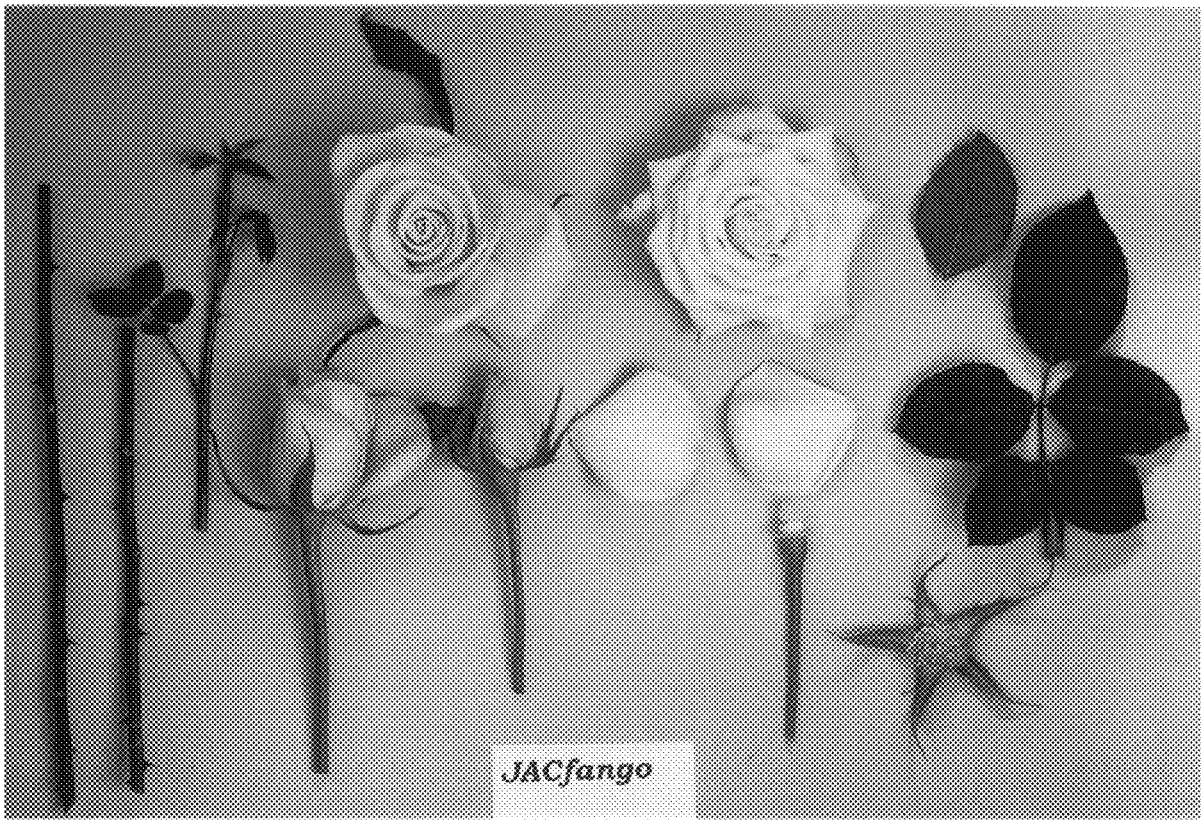
JACfango